US012616763B2

(12) United States Patent
     Kohen

(10) Patent No.: US 12,616,763 B2
(45) Date of Patent: May 5, 2026

(54) QUICK CONNECT DEVICE WITH DISINFECTION FEATURE AND LIGHTING FIXTURE FOR LIGHTING AND DISINFECTION

(71) Applicant: SKYX Platforms Corp., Johns Creek, GA (US)

(72) Inventor: Ran Roland Kohen, Aventura, FL (US)

(73) Assignee: SKYX Platforms Corp., Johns Creek, GA (US)

( * ) Notice: Subject to any disclaimer, the term of this patent is extended or adjusted under 35 U.S.C. 154(b) by 634 days.

(21) Appl. No.: 17/922,986

(22) PCT Filed: May 4, 2021

(86) PCT No.: PCT/US2021/030568
     § 371 (c)(1),
     (2) Date: Nov. 3, 2022

(87) PCT Pub. No.: WO2021/226018
     PCT Pub. Date: Nov. 11, 2021

(65) Prior Publication Data
     US 2023/0233719 A1        Jul. 27, 2023

Related U.S. Application Data

(60) Provisional application No. 63/019,954, filed on May 4, 2020.

(51) Int. Cl.
     *A61L 2/10*        (2006.01)
     *A61L 2/24*        (2006.01)
     (Continued)

(52) U.S. Cl.
     CPC .................. *A61L 2/10* (2013.01); *A61L 2/24* (2013.01); *A61L 2/26* (2013.01); *A61L 9/20* (2013.01);
     (Continued)

(58) Field of Classification Search
     None
     See application file for complete search history.

(56) References Cited

U.S. PATENT DOCUMENTS

|  |  |  |
|---|---|---|
| 484,911 A | 10/1892 | Green |
| 1,595,972 A | 8/1926 | DeReamer |
| (Continued) | | |

FOREIGN PATENT DOCUMENTS

| BR | 102017017951 A2 * | 4/2018 | ............... A61L 9/20 |
| CA | 2 549 756 A1 | 12/2007 | |
| | (Continued) | | |

OTHER PUBLICATIONS

For Canadian Patent Application No. 3,055,254: Office Action dated Nov. 21, 2023.

(Continued)

*Primary Examiner* — Andrew Smyth
(74) *Attorney, Agent, or Firm* — Fleit Intellectual Property Law; Paul D. Bianco

(57) ABSTRACT

Electrical connectors and fixtures, and more particularly, electrical plug and socket combinations allowing quick connection and mounting of electrical fixtures are provided with a disinfection feature for disinfecting air and/or surfaces. Additionally, lighting fixtures include or are retrofitted to provide both lighting and disinfection functions. The disinfection feature can be provided by any suitable source of UV radiation, such as an LED array. The emitted UV radiation is UV-A or FAR UV-C so that disinfection can occur regardless of whether a human is exposed to the emitted UV radiation or the emitted UV radiation is UV-C so that disinfection should only occur if there is no human exposure to the emitted UV radiation. Some electrical connectors and fixture can provide both types of emitted UV radiation, which are selectively actuatable.

19 Claims, 11 Drawing Sheets

(51) Int. Cl.
  *A61L 2/26* (2006.01)
  *A61L 9/20* (2006.01)
(52) U.S. Cl.
  CPC ........ *A61L 2202/11* (2013.01); *A61L 2202/14* (2013.01); *A61L 2202/25* (2013.01); *A61L 2209/111* (2013.01); *A61L 2209/12* (2013.01)

(56) References Cited

U.S. PATENT DOCUMENTS

| | | |
|---|---|---|
| 1,897,954 A | 2/1933 | D'Olier |
| 2,077,587 A | 4/1937 | Raymond |
| 2,308,016 A | 1/1943 | Mihalyi |
| 2,313,481 A | 3/1943 | Rendano |
| 2,494,428 A | 1/1950 | Buck |
| 2,673,966 A | 3/1954 | Larkin |
| 2,726,372 A | 12/1955 | Appleton |
| 2,728,895 A | 12/1955 | Quackenbush |
| 2,863,037 A | 12/1958 | Johnstone |
| 3,056,035 A | 9/1962 | Bernheim |
| 3,118,713 A | 1/1964 | Ellis |
| 3,159,444 A | 12/1964 | Stine |
| 3,193,636 A | 7/1965 | Daniels |
| 3,386,071 A | 5/1968 | Allen |
| 3,398,260 A | 8/1968 | Martens |
| 3,521,216 A | 7/1970 | Tolegian |
| 3,585,564 A | 6/1971 | Skjervoll |
| 3,648,002 A | 3/1972 | Du Rocher |
| 3,651,443 A | 3/1972 | Quilez |
| 3,668,603 A | 6/1972 | Burgess et al. |
| 3,798,584 A | 3/1974 | Person |
| 3,808,577 A | 4/1974 | Mathauser |
| 3,813,478 A | 5/1974 | Ervin |
| 3,855,564 A | 12/1974 | Dumas |
| 3,871,732 A | 3/1975 | Appleton |
| 4,059,327 A | 11/1977 | Vann |
| 4,079,244 A | 3/1978 | Bortoluzzi |
| 4,083,619 A | 4/1978 | McCormick et al. |
| 4,107,770 A | 8/1978 | Weber |
| 4,133,594 A | 1/1979 | Laverick et al. |
| 4,335,927 A | 6/1982 | Allen et al. |
| 4,448,388 A | 5/1984 | Dennis |
| 4,462,653 A | 7/1984 | Flederbach |
| 4,473,869 A | 9/1984 | De Widt |
| 4,588,248 A | 5/1986 | Moore |
| 4,629,843 A | 12/1986 | Kato et al. |
| 4,631,648 A | 12/1986 | Nilssen |
| 4,681,385 A | 7/1987 | Kruger et al. |
| 4,753,600 A | 6/1988 | Williams |
| 5,003,128 A | 3/1991 | Grondin |
| 5,034,869 A | 7/1991 | Choi |
| 5,173,053 A | 12/1992 | Swanson et al. |
| 5,250,874 A | 10/1993 | Hall et al. |
| 5,352,122 A | 10/1994 | Speyer |
| 5,362,122 A | 11/1994 | Reihl et al. |
| 5,438,216 A | 8/1995 | Juskey et al. |
| 5,442,532 A | 8/1995 | Boulos |
| 5,442,632 A | 8/1995 | Boulos et al. |
| 5,494,325 A | 2/1996 | Liu et al. |
| 5,494,326 A | 2/1996 | Hinds |
| 5,536,685 A | 7/1996 | Burward-Hoy |
| 5,551,882 A | 9/1996 | Whiteman |
| 5,562,458 A | 10/1996 | Stora et al. |
| 5,584,726 A | 12/1996 | Le Gallic et al. |
| 5,600,537 A | 2/1997 | Gordin |
| 5,622,873 A | 4/1997 | Kim et al. |
| 5,668,920 A | 9/1997 | Pelonis |
| 5,710,541 A | 1/1998 | Stanley |
| 5,754,408 A | 5/1998 | Derouiche |
| 5,777,391 A | 7/1998 | Nakamura et al. |
| 5,790,381 A | 8/1998 | Derouiche et al. |
| 5,803,590 A | 9/1998 | Wedell et al. |
| 5,808,556 A | 9/1998 | Nelson |
| 5,836,781 A | 11/1998 | Hyzin |
| 5,952,714 A | 9/1999 | Sano et al. |
| 5,962,810 A | 10/1999 | Glenn |
| 6,064,155 A | 5/2000 | Maya |
| 6,068,490 A | 5/2000 | Salzberg |
| 6,093,029 A | 7/2000 | Kwon et al. |
| 6,129,598 A | 10/2000 | Yu et al. |
| 6,135,800 A | 10/2000 | Majors |
| 6,170,967 B1 | 1/2001 | Usher et al. |
| 6,175,159 B1 | 1/2001 | Sasaki |
| 6,240,247 B1 | 5/2001 | Reiker |
| 6,241,559 B1 | 6/2001 | Taylor |
| 6,325,654 B1 | 12/2001 | Kerr |
| 6,332,794 B1 | 12/2001 | Tzeng Jeng |
| 6,340,790 B1 | 1/2002 | Gordin et al. |
| 6,364,716 B1 | 4/2002 | Seo |
| 6,366,733 B1 | 4/2002 | Reiker |
| 6,398,392 B2 | 6/2002 | Gordin et al. |
| 6,422,722 B1 | 7/2002 | Voltolina |
| 6,517,223 B2 | 2/2003 | Hsu |
| 6,595,782 B1 | 7/2003 | Hsiao |
| 6,598,990 B2 | 7/2003 | Li |
| 6,631,243 B2 | 10/2003 | Reiker |
| 6,648,488 B1 | 11/2003 | Pearce |
| 6,751,406 B2 | 6/2004 | Reiker |
| 6,793,383 B2 | 9/2004 | Wu |
| 6,821,089 B2 | 11/2004 | Bilskie |
| 6,837,754 B1 | 1/2005 | Walton |
| 6,930,250 B1 | 8/2005 | Drane |
| 6,962,498 B2 | 11/2005 | Kohen |
| 7,052,301 B2 | 5/2006 | Garcia et al. |
| 7,066,739 B2 | 6/2006 | McLeish |
| 7,192,303 B2 | 3/2007 | Kohen |
| 7,462,066 B2 | 12/2008 | Kohen |
| 7,467,881 B2 | 12/2008 | McMillen |
| 7,569,710 B1 | 8/2009 | Ozero |
| 7,706,757 B2 | 4/2010 | Luglio et al. |
| 7,723,862 B1 | 5/2010 | Spillman et al. |
| 7,878,691 B2 | 2/2011 | Liang |
| 7,891,841 B2 | 2/2011 | Levine |
| 8,123,378 B1 | 2/2012 | Ruberg et al. |
| 8,186,852 B2 | 5/2012 | Dassanayake et al. |
| 8,192,057 B2 | 6/2012 | Dassanayake et al. |
| 8,235,549 B2 | 8/2012 | Gingrich, III et al. |
| 8,277,082 B2 | 10/2012 | Dassanayake et al. |
| 8,348,678 B2 | 1/2013 | Hardisty |
| 8,354,768 B2 | 1/2013 | Cipriani |
| 8,357,016 B2 | 1/2013 | Schumacher |
| 8,419,218 B2 | 4/2013 | Dassanayake et al. |
| 8,449,137 B2 | 5/2013 | Dassanayake et al. |
| 8,558,413 B1 | 10/2013 | Lepard |
| D693,765 S | 11/2013 | Workman |
| 8,702,435 B2 | 4/2014 | Tajima |
| 8,854,796 B2 | 10/2014 | Wilcox |
| 8,888,326 B2 | 11/2014 | Hatch |
| 8,894,247 B2 | 11/2014 | Kim et al. |
| 8,979,347 B2 | 3/2015 | Holman |
| 9,328,910 B2 | 5/2016 | Lin et al. |
| 9,500,352 B2 | 11/2016 | Van Winkle |
| 9,644,824 B2 | 5/2017 | Dassanayake et al. |
| 9,702,535 B2 | 7/2017 | Dassanayake et al. |
| 9,901,039 B1 | 2/2018 | Dellerson et al. |
| 9,903,576 B2 | 2/2018 | Creasman et al. |
| 10,208,977 B2 | 2/2019 | Bhide |
| 10,266,998 B2 | 4/2019 | Apostolopoulos |
| 10,317,015 B2 | 6/2019 | Joye |
| 10,326,247 B2 | 6/2019 | Kohen |
| 10,326,274 B2 | 6/2019 | Kempen |
| 10,845,046 B2 | 11/2020 | Kohen |
| 11,196,216 B2 | 12/2021 | Kohen |
| 11,460,184 B2 | 10/2022 | Kohen |
| 2002/0060369 A1 | 5/2002 | Akram |
| 2002/0064380 A1 | 5/2002 | Reiker |
| 2002/0081107 A1 | 6/2002 | Reiker |
| 2003/0012027 A1 | 1/2003 | Hsu |
| 2003/0107891 A1 | 6/2003 | Kohen |
| 2004/0192415 A1 | 9/2004 | Luglio et al. |
| 2004/0223331 A1 | 11/2004 | Kao |
| 2005/0148241 A1 | 7/2005 | Kohen |
| 2006/0044789 A1 | 3/2006 | Curtis |
| 2006/0141842 A1 | 6/2006 | Sauer |
| 2006/0146527 A1 | 7/2006 | Vanderschuit |

(56) References Cited

U.S. PATENT DOCUMENTS

| | | |
|---|---|---|
| 2007/0105414 A1 | 5/2007 | Kohen |
| 2007/0167072 A1 | 7/2007 | Kohen |
| 2007/0258202 A1 | 11/2007 | Cooley et al. |
| 2008/0225531 A1 | 9/2008 | Shiller |
| 2009/0035970 A1 | 2/2009 | Kohen |
| 2009/0111322 A1 | 4/2009 | Roland |
| 2009/0129974 A1 | 5/2009 | McEllen |
| 2009/0135608 A1 | 5/2009 | Sell |
| 2009/0280673 A1 | 11/2009 | Kohen |
| 2009/0280675 A1 | 11/2009 | Zhou |
| 2010/0020550 A1 | 1/2010 | Kawashima |
| 2010/0214775 A1 | 8/2010 | Liang |
| 2010/0295473 A1 | 11/2010 | Chernel |
| 2010/0296285 A1 | 11/2010 | Chemel |
| 2010/0301769 A1 | 12/2010 | Chemel |
| 2011/0060701 A1 | 3/2011 | Verfuerth et al. |
| 2011/0134239 A1 | 6/2011 | Vadai et al. |
| 2012/0196471 A1 | 8/2012 | Guo |
| 2013/0040471 A1 | 2/2013 | Gervais et al. |
| 2013/0107536 A1 | 5/2013 | Hiraoka |
| 2014/0168944 A1 | 6/2014 | Osada et al. |
| 2014/0211487 A1 | 7/2014 | Spiro |
| 2014/0225731 A1 | 8/2014 | Gouveia |
| 2014/0268790 A1 | 9/2014 | Chobot et al. |
| 2014/0301071 A1 | 10/2014 | Jørgensen |
| 2015/0009666 A1 | 1/2015 | Keng et al. |
| 2015/0009676 A1 | 1/2015 | Danesh |
| 2015/0044040 A1 | 2/2015 | Oda et al. |
| 2015/0085500 A1 | 3/2015 | Cooper et al. |
| 2016/0053952 A1 | 2/2016 | Kuti et al. |
| 2016/0069556 A1 | 3/2016 | Li |
| 2016/0074574 A1 | 3/2016 | Welsch |
| 2016/0131358 A1 | 5/2016 | Spiro |
| 2016/0255697 A1 | 9/2016 | Bhide |
| 2017/0105265 A1 | 4/2017 | Sadwick |
| 2017/0234319 A1 | 8/2017 | Seccareccia |
| 2017/0248148 A1 | 8/2017 | Kohen |
| 2018/0115131 A1* | 4/2018 | Kohen ............... H01R 13/7038 |
| 2018/0169279 A1 | 6/2018 | Randers-Pehrson |
| 2019/0083667 A1* | 3/2019 | Hawkins ................. A61N 5/06 |
| 2019/0224350 A1* | 7/2019 | Marry ...................... A61N 5/06 |
| 2019/0312396 A1 | 10/2019 | Kohen |
| 2020/0018469 A1 | 1/2020 | Kohen |
| 2020/0056773 A1 | 2/2020 | Kohen |
| 2020/0144766 A1 | 5/2020 | Kohen |
| 2021/0296819 A1 | 9/2021 | Kohen |
| 2022/0190518 A1 | 6/2022 | Kohen |
| 2023/0204200 A1 | 6/2023 | Kohen |
| 2023/0233719 A1 | 7/2023 | Kohen |
| 2024/0088608 A1 | 3/2024 | Kohen |
| 2024/0243538 A1 | 7/2024 | Kohen |

FOREIGN PATENT DOCUMENTS

| | | | |
|---|---|---|---|
| CN | 2586059 Y | | 11/2003 |
| CN | 1582518 A | | 2/2005 |
| CN | 1728475 A | | 2/2006 |
| CN | ZL 01 8 23877.7 | | 11/2007 |
| CN | 10195268 A | | 12/2007 |
| CN | 101095268 A | | 12/2007 |
| CN | 102483213 A | | 5/2012 |
| CN | 202253241 U | | 5/2012 |
| CN | 202501418 U | | 10/2012 |
| CN | 102870307 A | | 1/2013 |
| CN | 103782384 A | * 5/2014 | ............... A61L 6/20 |
| CN | 104033399 A | | 9/2014 |
| CN | 203934061 U | | 11/2014 |
| CN | 204879746 U | | 12/2015 |
| CN | 105674223 A | | 6/2016 |
| CN | 205790597 U | * 12/2016 | |
| CN | 107211515 A | | 9/2017 |
| CN | 115668663 A | | 1/2023 |
| DE | 19849101 A1 | | 4/1999 |
| DE | 29923352 U1 | | 8/2000 |
| DE | 20203467 U1 | | 6/2002 |

| | | | |
|---|---|---|---|
| EP | 0704934 A2 | | 4/1996 |
| EP | 1024559 A2 | | 8/2000 |
| EP | 1456914 A1 | | 9/2004 |
| EP | 1789984 A2 | | 5/2007 |
| EP | 3295525 A1 | | 5/2016 |
| IL | 126246 | | 8/2001 |
| JP | 53-26859 | | 8/1978 |
| JP | 2003-016831 A | | 1/2003 |
| JP | 2003-16831 A | | 1/2003 |
| JP | 2004-320228 A | | 11/2004 |
| JP | 2008166071 A | | 7/2008 |
| JP | 2010129489 A | | 6/2010 |
| JP | 5331043 B2 | | 10/2013 |
| JP | 53311043 B2 | | 10/2013 |
| JP | 7291880 | | 6/2023 |
| RU | 2009583 C1 | | 3/1994 |
| RU | 2275720 C2 | | 4/2006 |
| RU | 2011122686 | | 10/2012 |
| RU | 2526853 | | 8/2014 |
| WO | 00/16442 | | 3/2000 |
| WO | 01/01047 A1 | | 1/2001 |
| WO | 03/044906 A1 | | 5/2003 |
| WO | 2005053100 A2 | | 6/2005 |
| WO | 2005/074087 A1 | | 8/2005 |
| WO | 2006031853 A2 | | 3/2006 |
| WO | 2006060772 A2 | | 6/2006 |
| WO | 2010/064914 A1 | | 6/2010 |
| WO | 2011/005526 A2 | | 1/2011 |
| WO | 2011/020231 A1 | | 2/2011 |
| WO | 2011/134709 A2 | | 11/2011 |
| WO | 2013/159833 A1 | | 10/2012 |
| WO | 2012/167320 A1 | | 12/2012 |
| WO | 2016/009181 A1 | | 1/2016 |
| WO | 2016054159 A1 | | 4/2016 |
| WO | 2016/144795 A1 | | 9/2016 |
| WO | 2016/183354 | | 11/2016 |
| WO | 2016183354 A1 | | 11/2016 |
| WO | 2018/204313 A1 | | 5/2018 |
| WO | 2018/165646 | | 9/2018 |
| WO | 2018/165646 A1 | | 9/2018 |
| WO | WO-2018165058 A1 * | 9/2018 | ............. H01R 24/38 |
| WO | 2018/165058 | | 10/2018 |
| WO | 2018/195068 | | 10/2018 |
| WO | 2018/195068 A1 | | 10/2018 |
| WO | 2019/222259 A1 | | 11/2019 |
| WO | 2020/039215 | | 2/2020 |
| WO | 2020/039215 A1 | | 2/2020 |
| WO | 2020/172390 A1 | | 8/2020 |
| WO | 2021/174187 A1 | | 9/2021 |
| WO | 2021/226018 A1 | | 11/2021 |
| WO | 2022/150645 A1 | | 7/2022 |
| WO | 2022/159853 A1 | | 7/2022 |

OTHER PUBLICATIONS

For Canadian Patent Application No. 3,055,772: Office Action dated Nov. 15, 2023.

For Canadian Patent Application No. 3,062, 157: Office Action dated Nov. 23, 2023.

For Canadian Patent Application 2,985,821: Office Action dated Jun. 16, 2023 Response filed Oct. 16, 2023.

Notice of Allowance dated Oct. 26, 2023 for U.S. Appl. No. 17/432,155.

International Search Report, Written Opinion, International Preliminary Report on Patentability for PCT/US2004/039399 filed Nov. 22, 2004.

International Search Report, Written Opinion, International Preliminary Report on Patentability for PCT/US2005/032661 filed Sep. 14, 2005.

International Search Report, Written Opinion, International Preliminary Report on Patentability for PCT/US2005/043934 filed Dec. 2, 2005.

International Search Report, Written Opinion, International Preliminary Report on Patentability for PCT/US2015/53138 filed Sep. 30, 2015.

International Search Report and Written Opinion for PCT/US2016/32170 filed May 12, 2016.

(56)                    References Cited

OTHER PUBLICATIONS

European Search Report for EP05796234 dated Nov. 5, 2007 related to WO2006/031853).
International Search Report for PCT/IL01/01078 filed Nov. 22, 2001.
Office Action for U.S. Appl. No. 15/515,664, dated Sep. 10, 2019.
International Preliminary Report on Patentability dated Sep. 10, 2019 for PCT/US2018/020987, filed Mar. 5, 2018.
International Search Report dated Jul. 6, 2018 for PCT/US2018/027956 filed Apr. 17, 2018.
Written Opinion Jul. 6, 2018 for PCT/US2018/027956 filed Apr. 17, 2018.
International Search Report dated May 17, 2018 for PCT/US2018/021919 filed Mar. 12, 2018.
Witten Opinion for PCT/US2018/021919 filed Mar. 12, 2018.
International Preliminary Report on Patentability dated Sep. 10, 2019 for PCT/US2018/021919.
International Search Report dated Aug. 13, 2018 for PCT/US2018/030372 filed May 1, 2018.
Written Opinion dated Aug. 13, 2018 for PCT/US2018/030372 filed May 1, 2018.
International Preliminary Report on Patentability dated Oct. 22, 2019 for PCT/US2018/027956.
Response filed Jan. 17, 2019, in U.S. Appl. No. 15/573,606.
European Search Report for Application No. 16793548.5 dated Feb. 14, 2019.
Second Office Action for Chinese Patent Application No. 201580063483.2, dated Jun. 14, 2019 (with translation of 1 cover page).
Office Action dated Sep. 1, 2022 for Canadian Application No. 2,985,821.
International Preliminary Report on Patentability and Written Opinion dated Nov. 8, 2022 for PCT/US2021/030568, filed May 4, 2021 (English translation.
Office Action dated Nov. 4, 2022 for European Patent Application No. 16 793 548.5.
International Preliminary Report on Patentability, dated Aug. 30, 2022, for PCT/US2021/020233.
Response to Office Action filed Nov. 3, 2022 for Indian Patent Application No. 201937046706.
International Preliminary Report on Patentability dated Sep. 10, 2019 with Written Opinion for PCT/US2018/021919, filed Mar. 12, 2018.
International Search Report and Written Opinion for PCT/US2021/030568, filed May 4, 2021.
1 Office Action dated Dec. 20, 2023 for Canadian Patent Application No. 3,130,493.
International Preliminary Report on Patentability dated Nov. 5, 2019 for International Application No. PCT/US2018/030372 filed May 1, 2018, 6 pages.
Written Opinion for International Application No. PCT/US2018/030372 filed May 1, 2018, 5 pages.
For Chinese Patent Application No. 201580063483.2 (national stage of PCT/US2015/053138): Third Office Action, dated Sep. 18, 2019 (with English translation) Response to Third Office Action, dated Dec. 2, 2019 (13 pages).
For Chinese Patent Application No. 201580063483.2 (national stage of PCT/US2015/053138): Response to First Office Action, dated Feb. 11, 2019 (9 pages) Response to Second Office Action, dated Aug. 26, 2019 (12 pages).
For Chinese Patent Application No. 2016800404661 (national stage of PCT/US2016/032170): Second Office Action, dated Dec. 2, 2019 (3 pages) Search Report, dated Nov. 24, 2019 (2 pages).
For Indian Patent Application No. 201717013438 (National Stage of PCT/US2015/053138): First Examination Report, dated Dec. 13, 2019 (6 pages).
International Search Report dated May 25, 2020, for PCT/US2020/019010 filed Feb. 20, 2020.
Written Opinion for PCT/US2020/019010 filed Feb. 20, 2020.
Communication dated Nov. 17, 2020 for European Patent Application No. 187636469.

Supplemental European Search Report dated Oct. 30, 2020 for European Patent Application No. 187636469.
Office Action dated Jan. 28, 2022 for U.S. Appl. No. 17/240,102, filed Apr. 26, 2021.
Office Action dated Dec. 13, 2021 issued by the European Patent Office for Application No. 15 846 948.6.
Response to Office Action, dated Jan. 12, 2022, for Mexican Patent Appl. No. MX/A/2017/004137.
First Office Action dated Aug. 13, 2020 for Chinese Application No. 2018800295358.
Search Report dated Aug. 7, 2020 for Chinese Application No. 2018800295358.
For U.S. Appl. No. 15/515,664, filed Mar. 30, 2017: Responses filed Jan. 10, 2020, Sep. 10, 2020, Jul. 27, 2021 Notice of Allowance dated Aug. 23, 2021.
Extended Search Report dated Oct. 17, 2022 for Application No. 20768521.7.
Office Action for U.S. Appl. No. 16/491,321, dated Apr. 21, 2020.
First Notification of Office Action dated Nov. 19, 2020, for Chinese Application No. 2018800333913, National Stage of PCT/US2018/027956 10 pages (with partial English translation).
First Office Action dated Dec. 23, 2020, for Israeli Patent Application No. 255549, National Stage of PCT/US2016/32170 7 pages.
Office Action dated Jan. 27, 2021, for U.S. Appl. No. 15/515,664, filed Mar. 30, 2017 67 pages.
European Search Report dated Oct. 21, 2020 for EP 18764255.8.
For Brazilian Patent Application No. BR 11 2017 024224-9 (National Stage of PCT/US2016/032170): Response filed Oct. 14, 2020.
International Search Report and Written Opinion dated Jun. 17, 2021, for PCT/US2021/020233.
International Search Report and Written Opinion for PCT/US2018/21919 filed Mar. 12, 2018.
International Search Report and Written Opinion for PCT/US2018/20987 filed Mar. 5, 2018.
European Search Report dated Jul. 3, 2018 for Application No. 15846948.6-1004/3212939.
Notice of Allowance dated Mar. 14, 2024 for Canadian Patent Application No. 2,985,821.
Ex parte Quayle Office Action dated May 16, 2023, for U.S. Appl. No. 17/432,155.
International Preliminary Report on Patentability dated Nov. 14, 2017 for PCT/US2016/032170 filed May 12, 2016.
First Examination Report (FER) dated Feb. 13, 2022, and Response, dated Aug. 18, 2022, for Indian Application No. 201937049201 (17 pages).
For European Patent Application EP18764255.8: Office Action dated May 10, 2024.
Chinese Search Report dated Feb. 18, 2019, for Patent Application No. 2016800404661.
First Office Action dated Feb. 27, 2019, from Chinese Patent Office for Patent Application No. 201680040466.1.
Office Action dated Jun. 28, 2024 for Mexican Patent Application MX/a/2021/010076 filed Feb. 20, 2020.
Office Action dated Feb. 1, 2024 for Israeli Patent Application No. 269246 (with English summary).
Search Report dated Feb. 20, 2024 for European Patent Application No. 21759787.1.
Office Action dated Feb. 6, 2024 for Japanese Patent Application No. 2021-548174.
Office Action dated Jan. 26, 2022, for European Patent Application No. 18 763 646.9 (National Stage of PCT/US2018/020987) (6 pages).
English translation of Search Report from Chinese Patent Office for Application No. 201580063483.2 dated Sep. 11, 2018.
Office Action from Chinese Patent Office for Application No. 201580063483.2 dated Sep. 25, 2018 (with English translation).
International Search Report dated Aug. 4, 2021 for PCT/US2021/030568, filed May 4, 2021.
Written Opinion dated Aug. 4, 2021 for PCT/US2021/030568, filed May 4, 2021.
International Preliminary Report on Patentability dated Jul. 4, 2023 for PCT/US2022/011701.

(56)　　　　References Cited

OTHER PUBLICATIONS

International Preliminary Report on Patentability dated Aug. 10, 2021 with Written Opinion for PCT/US2020/019010.
For Russian Application No. 2021127449 filed Feb. 20, 2020: Russian Office Action dated May 16, 2023 Russian Search Report dated May 11, 2023.
Oficial Communication dated Aug. 22, 2023 for Inian Patnt Application No. 201937040845.
Notice of Allowance dated Nov. 4, 2021 for Japanese Patent Application No. 2018-511347 (with English translation).
Notification of Publication dated Nov. 11, 2021 for Chinese Application No. 202080022559.8 (with English translation).
First Office Action dated Nov. 3, 2021 for Canadian Patent Application No. 2,963,134.
Office Action for Canadian Patent Application No. 3,169,781 dated Feb. 5, 2024 (4 pages).
Response submitted for Canadian Patent Application No. 3,055,254, dated Mar. 21, 2024 (19 pages).
For Russian Patent Application 2017142137 (national Stage of PCT/US2016/032170): Prosecution history including decision to grant dated Oct. 25, 2019.
Office Action issued by the European Patent Office dated Dec. 19, 2019 for Application No. 16 793 548.5-1201.
First Examination Report for Mexican Patent Application No. MX/a/2017/004137, dated Aug. 10, 2021.
First Office Action dated Sep. 2, 2020 for Chinese Application No. 201880030051.5 with translation of cover page (12 pages).
Response to First Examination Report, filed Sep. 4, 2020 for Indian Patent Application No. 201717013438, National Stage of PCT/US2015/053138.
Office Action dated Aug. 3, 2020, for European Patent Application No. 16793548.5 (Regional Stage of PCT/US2016/032170).
International Search Report and Written Opinion dated Mar. 23, 2022 for PCT/US2022/011701 filed Jan. 7, 2022.
Notification of Reasons for Refusal, Office Action dated Jan. 4, 2022, for Japanese Patent Appl. No. 2019-548872 (18 pages with English translation).
Office Action dated Nov. 24, 2022 for Israeli Application No. 269246 and translation of Summary.
Office Action dated Jan. 5, 2023 for U.S. Appl. No. 17/432,155, filed Aug. 19, 2021.
International Preliminary Report on Patentability dated Jul. 20, 2023 for PCT/US2022/013598 filed Jan. 25, 2022.
International Search Report with Written Opinion dated Jul. 6, 2018 for PCT/US2018/027956.
Office Action dated Sep. 18, 2018 in U.S. Appl. No. 15/573,606.
First Office Action dated Oct. 23, 2020 for Chinese Application No. 2018800402400.
Decision of Refusal (Office Action) dated Sep. 13, 2022 for Japanese Patent Application No. 2019-548272.
Office Action dated Oct. 28, 2022 for European Patent Application No. 18 764 255.8.
For Japanese Application No. 2019-548872: Notification of Reasons for Refusal dated Dec. 12, 2022.
Notification on Publication of Patent, dated Feb. 3, 2023, for Chinese Patent Application No. 202180031100.9.
International Search Report with Written Opinion dated Aug. 13, 2018 for PCT/US2018/030372.
Office Action dated Sep. 25, 2018 from Chinese Patent Office for Application No. 201580063483.2.
Technical Examination Report dated Mar. 13, 2023 for Brazilian Application No. BR112017024224-9.
IAEI, When continuity snaps, May-Jun. 2015.

IAEI, Supports reinforce our safety, Hanging Support Systems, Mar.-Apr. 2015.
Amendment and Statement of Argument filed with the Japanese Patent Office on Aug. 6, 2021 for Japanese Patent Application No. 2018-511347.
Notification of Reasons for Refusal Office Action dated Jan. 4, 2022 for Japanese Patent Application 2019-548272 (8 pages with English translation).
Notice of Allowance dated Jul. 8, 2020 for U.S. Appl. No. 16/609,875.
International Search Report for PCT/IL99/00499 filed Sep. 14, 1999.
European Search Report for EP 01 27 4757 dated Mar. 28, 2006.
Australian Examiner's First Report on Patent Application AU 2002221000.
Indian First Examination Report dated Jun. 24, 2010 for Indian Application No. 1677/KOLNP/2006.
New Zealand Examination Report for NZ Patent Application No. 533697 dated May 9, 2007.
For Chinese Patent Application No. 01823877.7: Notice of Allowance dated Oct. 17, 2006 Second Office Action dated Apr. 6, 2007 First Office Action dated Jul. 4, 2006.
For Brazilian Appl. No. BR112019023032-7 (national stage of PCT/US2018/030372): Technical and Search Report, dated Sep. 13, 2022 Response, dated Dec. 14, 2022.
For Brazilian Patent Application No. BR 11 2017 024224-9 (National Stage of PCT/US2016/032170): Amended claims filed May 7, 2019 Response filed Jun. 19, 2023.
Publication issued in the Official Gazette from Mexican Patent Application MX/a/2017/004137 dated Feb. 13, 2018, 3 pages.
International Search Report dated Jul. 18, 2016 for International Application No. PCT/US2016/032170 filed May 12, 2016.
Written Opinion for for International Application No. PCT/US2016/032170 filed May 12, 2016.
Japanese Notice of Allowance dated Mar. 16, 2023 for Japanese Patent Application No. 2019-548272.
Final Office Action for U.S. Appl. No. 15/515,664, dated Mar. 10, 2020.
Office Action for US Patent Appl. Nol. U.S. Appl. No. 16/443,207, dated Mar. 11, 2020.
For U.S. Appl. No. 17/907,753 Office Action dated May 29, 2024.
Written Opinion dated May 25, 2020 for PCT/US2020/019010 filed Feb. 20, 2020.
International Search Report and Written Opinion dated Apr. 8, 2022 for PCT/US2022/013598 filed Jan. 25, 2022.
For U.S. Appl. No. 16/605,994: Notice of Allowance dated Jun. 29, 2020.
First Examination Report dated Jun. 2, 2020 for Indian Patent No. 201717042509 filed Nov. 27, 2017.
Notice of Allowance dated Feb. 2, 2021 for U.S. Appl. No. 16/443,207.
For Mexican Patent Application No. MX/A/2017/014475 (national Stage of PCT/US2016/032170): Office Action dated Feb. 3, 2021, with English translation.
First Examination Report dated Mar. 25, 2021 for Indian Patent Application No. 201937040845.
Chinese Patent Application No. 2018800402400 (National Stage of PCT/US2018/030372): Second Office Action, dated Jun. 1, 2021.
Office Action dated Mar. 27, 2023 for Korean Patent Application No. 10-2017-7035630.
Notice of Allowance dated May 31, 2022 for US Patent Application No. 17/240, 102.

* cited by examiner

QUICK CONNECT DEVICE WITH DISINFECTION FEATURE AND LIGHTING FIXTURE FOR LIGHTING AND DISINFECTION

FIELD OF THE DISCLOSURE

The disclosure relates to electrical connectors and fixtures, and more particularly, to an electrical plug and socket combination allowing quick connection and mounting of electrical fixtures and having a disinfection feature for disinfecting air and/or surfaces. The disclosure also relates to a lighting fixture that includes or is retrofitted to provide both lighting and disinfection functions.

RELATED PATENTS AND APPLICATIONS

This disclosure relates to U.S. Patent Application No. 62/486,132 filed Apr. 17, 2017; PCT International Patent Application No. PCT/US18/27956 filed Apr. 17, 2018 (published as WO 2018/195068 A1): U.S. Patent Application No. 62/467,176 filed Mar. 5, 2017: PCT International Patent Application No. PCT/US2016/032170 filed May 12, 2016 (published as WO 2016/183354 A1): U.S. Pat. No. 7,462,066 filed Mar. 20, 2007:7,192,303 filed Dec. 2, 2004; and 6,962,498 filed Dec. 12, 2001; and to U.S. Patent Application Publication No. 2009/0280673 filed Dec. 2, 2005: U.S. Provisional Applications 62/160,585 filed May 12, 2015; 62/308,718, filed Mar. 15, 2016; 62/467,176 filed Mar. 5, 2017:62,470,170 filed Mar. 10, 2017: 62/515,464, filed Jun. 5, 2017; and U.S. Patent Application No. 62/807,889 filed Feb. 20, 2019, the contents of all of which are hereby incorporated by reference herein, in their entirety.

BACKGROUND OF THE DISCLOSURE

The use of UV light for disinfecting is generally known. However, some UV wavelengths have no effect on killing microorganisms. Such emitted wavelengths waste energy and can be harmful to humans over time. Such lamps also need a high voltage power supply, which can create safety issues.

The patents identified above in the Related Patents and Applications Section disclose various embodiments of quick connect devices and lighting fixtures. In particular, these related patents and applications disclose various embodiments of plug and socket combinations that permit quick connection of an electrical fixture or appliance at an electrical junction box on a wall or ceiling. The socket is secured on the wall or ceiling near electrical power supply wiring and includes female receptacles which receive male electrical prongs carried on the plug. The electrical fixture is secured to the plug. In addition to the quick electrical connection provided by this plug and socket combination, a mechanical connection between the plug and socket carries the mechanical load of the electrical fixture.

This disclosure sets forth improvements related to various embodiments of the plug and socket combinations in the related patents and applications having a disinfection feature. Lighting fixtures that include or are retrofitted to provide both lighting and disinfection functions are also disclosed.

SUMMARY

One aspect of the disclosure relates to a canopy for a light fixture, with the canopy including a connector for coupling to the light fixture, a plug of a quick connect device, and a plurality of emitters emitting UVA and/or FAR UVC radiation. The plurality of emitters can include a coupler for supplying electricity thereto and the canopy can include an aperture for accommodating the coupler. In an embodiment, the plurality of emitters forms a ring on a periphery of the canopy. The plurality of emitters can be an array of LEDs that emits UVA radiation.

The canopy can include an antenna and/or sensor array to control selective activation of the plurality of emitters and/or illumination of the light fixture. In an embodiment, the plurality of emitters is removably attached to the canopy. The removable attachment can be achieved with at least one of a screw connection, a hook and loop fastener, a magnetic coupling, and an adhesive. The removable attachment can be at any location of the canopy, but in an exemplary embodiment, the removable attachment is at a base of the canopy.

Another aspect of the disclosure relates to a smart quick connect device for electrically and mechanically connecting an electrical fixture, the device comprising a socket and a plurality of emitters emitting UV radiation. In an embodiment, the plurality of emitters includes a first plurality of emitters in the form of a ring along a periphery of the smart quick connect device and a second plurality of emitters centrally located within the ring on the smart quick connect device.

The first and second plurality of emitters can be separately activatable, with the first plurality of emitters emitting UVA and/or FAR UVC radiation when activated and the second plurality of emitters emitting UVC radiation when activated. In an embodiment, the first plurality of emitters comprises a first array of LEDs and the second plurality of emitters comprises a second array of LEDs. The first array of LED's can emit UVA radiation when activated.

In some embodiments, the smart quick connect device further comprises at least one sensing unit for wirelessly communicating a sensed condition and/or for wireless receiving a signal. The at least one sensing unit can include a sensor for wirelessly receiving a command signal to control the device and/or an associated electrical fixture, with the sensor controlling activation of the first and second plurality of emitters. The command signal can result from the sensed condition. The at least one sensing unit can include a sensor for sensing an environmental condition, with activation of the first and second plurality of emitters determined by the sensed environmental condition. In some embodiments, the smart quick connect device further comprises a speaker/microphone assembly.

Another aspect of the disclosure relates to a smoke and $CO_2$ detector with a plurality of emitters emitting UVA and/or FAR UVC radiation when activated. In some embodiments, the plurality of emitters forms a ring on a periphery of the detector. In an exemplary embodiment, the plurality of emitters is an array of LEDs, with the array of LEDs emits UVA radiation when activated.

The detector can further comprise a plurality of UVC emitters emitting UVC radiation when activated, with the plurality of emitters and plurality of UVC emitters separately activatable.

Another aspect of the disclosure relates to a recessed lighting fixture with a housing and a trim, with the trim including at least one emitter emitting UVA radiation. The at least one emitter can be a ring of emitters emitting UVA radiation.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings (which form an integral part of the description and are to be read in conjunction therewith, and in which like reference numerals are employed to designate identical components in the various views) wherein.

DETAILED DESCRIPTION

Figure 1:
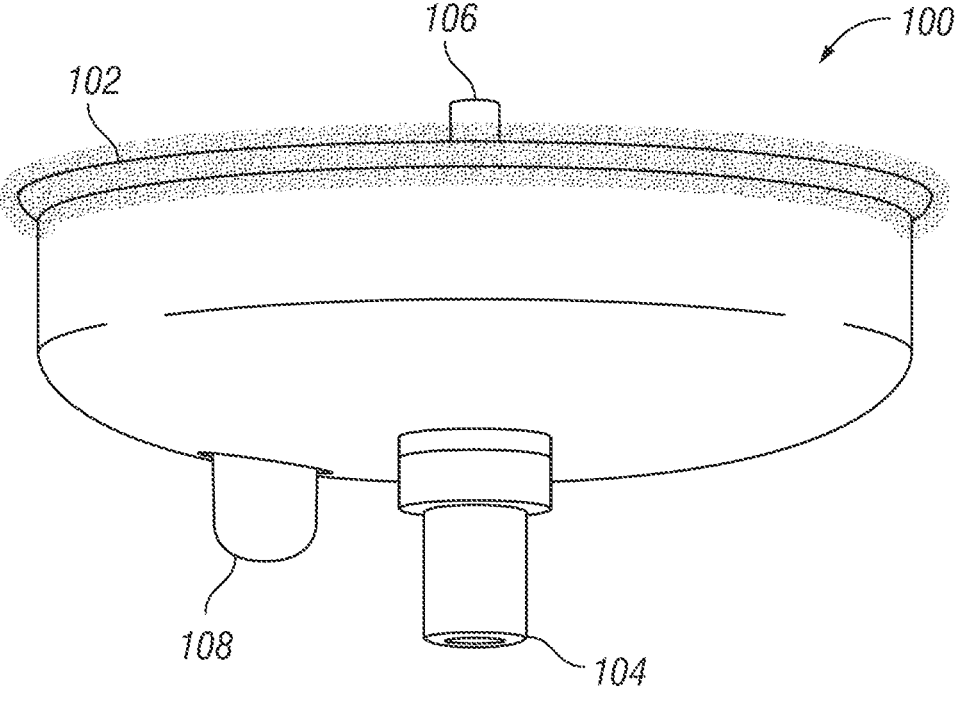
FIG. 1 depicts a canopy according to the disclosure that includes a plug of a quick connect device and a UV disinfecting ring.

As required, embodiments are disclosed herein; however, it is to be understood that the disclosed embodiments are merely examples and that the devices and methods described below can be embodied in various forms. Therefore, specific structural and functional details disclosed herein are not to be interpreted as limiting, but merely as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

The disclosure herein relates to the inventor's prior work, such as that set forth above in the documents identified in the Related Patents and Applications section, the contents of each of which are herein incorporated in their entirety by reference. In this regard, the plug and/or socket can include a sensing unit for at least one of wirelessly communicating a sensed condition and wirelessly receiving a signal as disclosed in PCT International Patent Application No. PCT/

US2016/032170 filed May 12, 2016 and PCT International Patent Application No. PCT/US2018/020987 filed Mar. 5, 2018.

A "quick connect device" for installing electrical fixtures comprises the combination of a plug and mating socket, which is also known as a receptacle. The plug and mating socket of the device function to both establish an electrical connection between an electrical fixture and electrical supply wiring, and mechanically support the fixture on a surface or base, typically a wall, ceiling or floor surface. As used herein, the term "fixture" or "electrical fixture" means any fixture or appliance such as a lighting fixture, ceiling fan, television camera, security device or any other device which is powered by electricity supplied by electrical wiring, and which requires a mechanical connection to support or suspend the fixture. The plug is fixedly secured to an electrical fixture, while the socket is secured to either the surface (e.g., wall, ceiling or floor) on which the fixture is to be mounted, or to an electrical junction box. The structure, function, and operation of the plug and mating socket, generally, have already been detailed in, for example, the patents and application incorporated by reference herein.

Referring for example to the incorporated reference published as PCT/US2016/032170 (the "'170 publication"), a quick connect device 20 for installing electrical fixtures comprises the combination of a plug 22 and mating socket 24. A detailed description of the structure and function of a plug 22 and spindle assembly 34 is provided in the '170 publication and other incorporated references. As in the '170 publication, one or more sensors or other receiving/input or transmitting/output electronic or electrical devices 48, 50) (hereinafter 'sensors') can be associated with either plug 22 or socket 24. Socket 24 is known, as disclosed in the incorporated references, and as codified in the U.S. National Electric Code.

Devices of the disclosure can be provided with or attached to electronic sensors and/or processors, transmitters and/or receivers, and other electronic circuits, and which may be deemed 'smart' devices, or device of the disclosure may be associated with power consuming devices such as lights or fans, which may or may not include 'smart' electronics or components, or other electronics which are unrelated to the operation of the device itself.

This disclosure relates to combining the above-described technology with a source of electromagnetic radiation, primarily ultraviolet (UV) rays for disinfection of air and surfaces exposed to the radiation. Wavelengths of visible light range between 400 and 700 nanometers (nm) and are generally not considered efficient for germicidal disinfection. UV wavelengths are in the range of 200 nm to 390 nm and have optimal UV germicidal action at 254-265 nm. For UV sterilization, only UV-C(100-280 nm) has high enough energy to effectively kill microorganisms. Although UV-C can immediately kill pathogens. UV-C generally should be used without humans present (or the exposure of humans should limited to no more than a certain number of minutes per day) because of potential adverse health consequences.

UV-A (315 to 400 nm band) energy or short-wavelength energy in the violet or blue range destroy pathogens over longer exposure times. The typical product mixes violet LEDs and white LEDs in a luminaire and only uses the violet LEDs during periods when a space is being disinfected. The mixed white and violet light is still usable for humans working in the space. The violet energy destroys pathogens over long exposure times.

Although there is evidence that FAR UV-C(207-222 nm) is considered both safe to humans and effective in killing microorganisms, FAR UV-C does not have the extensive data supporting the safety and efficacy that UV-A has.

FIG. 1 shows a canopy 100 that includes a disinfecting ring 102 that emits UV radiation for disinfection. Although disinfecting ring 102 can include any suitable source of UV radiation, in an exemplary embodiment the UV radiation source is an LED array. In one embodiment, the emitted UV radiation is UV-A or FAR UV-C so that disinfecting ring 102 can emit the radiation regardless of whether a human is exposed to the emitted UV radiation (e.g, an occupied room) or not (e.g, an unoccupied room). In another embodiment, the emitted UV radiation is UV-C so that disinfecting ring 102 should only emit the radiation if there is no human exposure to the emitted UV radiation (e.g, an occupied room).

A user selected light fixture would be attached to shaft 104 to provide illumination. Canopy 100 includes plug 106 (as set forth in the 170 publication and other incorporated by reference related patents and applications set forth above) that removably connects to a socket of a quick connect device (again as set forth in the 170 publication and other incorporated by reference related patents and applications set forth above). Canopy 100 can also include an antenna and/or sensor array 108 to control selective activation of disinfecting ring 102 and/or illumination of the light fixture (and/or a ceiling fan if incorporated in the light fixture).

Disinfecting ring 102 can be integrally formed with canopy 100 or can be removably attached to canopy 100. Removable attachment would be particularly useful to replace disinfecting ring 102 (for example to change the wavelength or replace) or to retrofit a canopy 100 with disinfecting ring 102.

Figure 2:
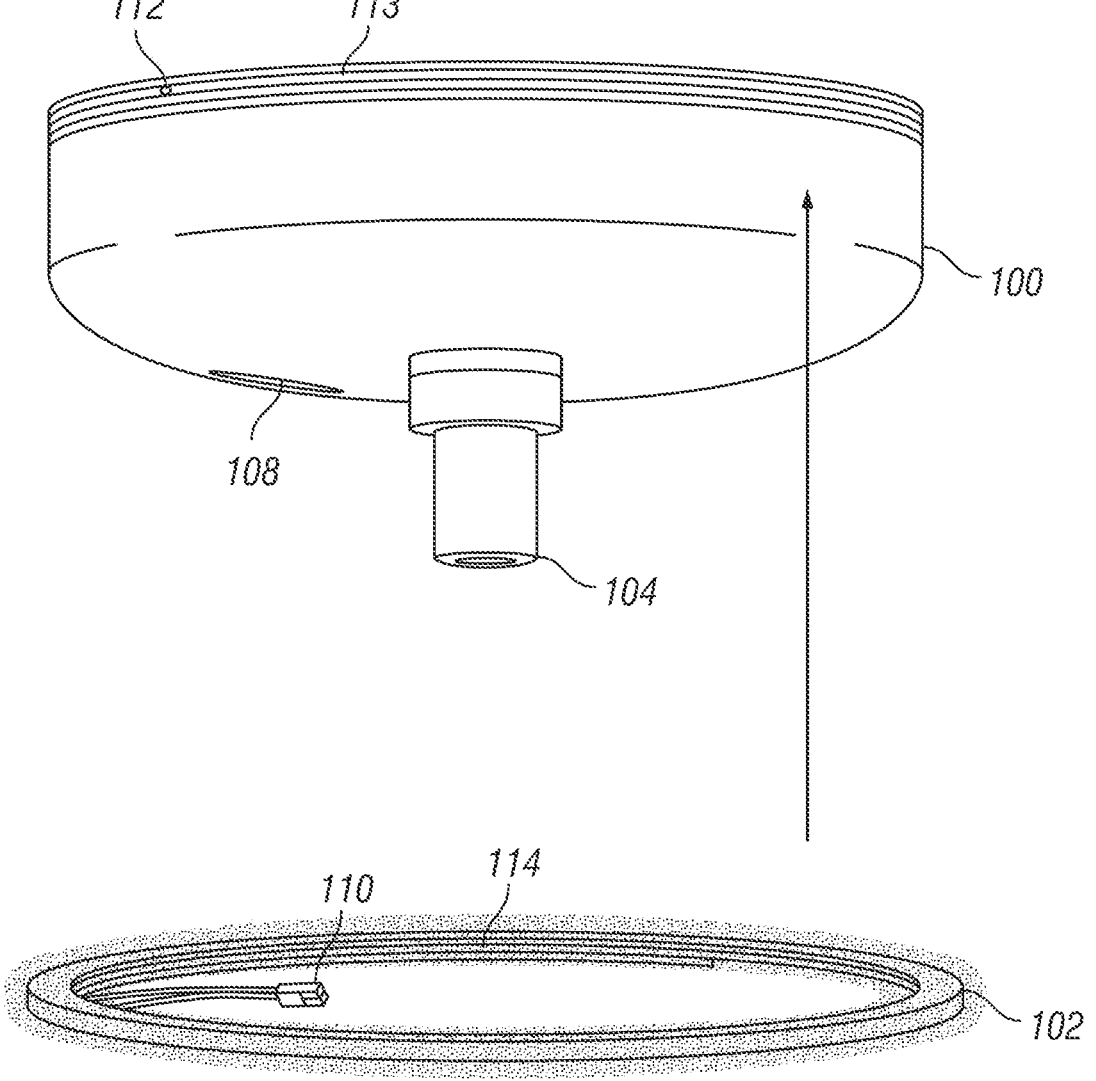
FIG. 2 depicts a first exemplary mechanism for attaching the UV disinfecting ring.
Figure 3:
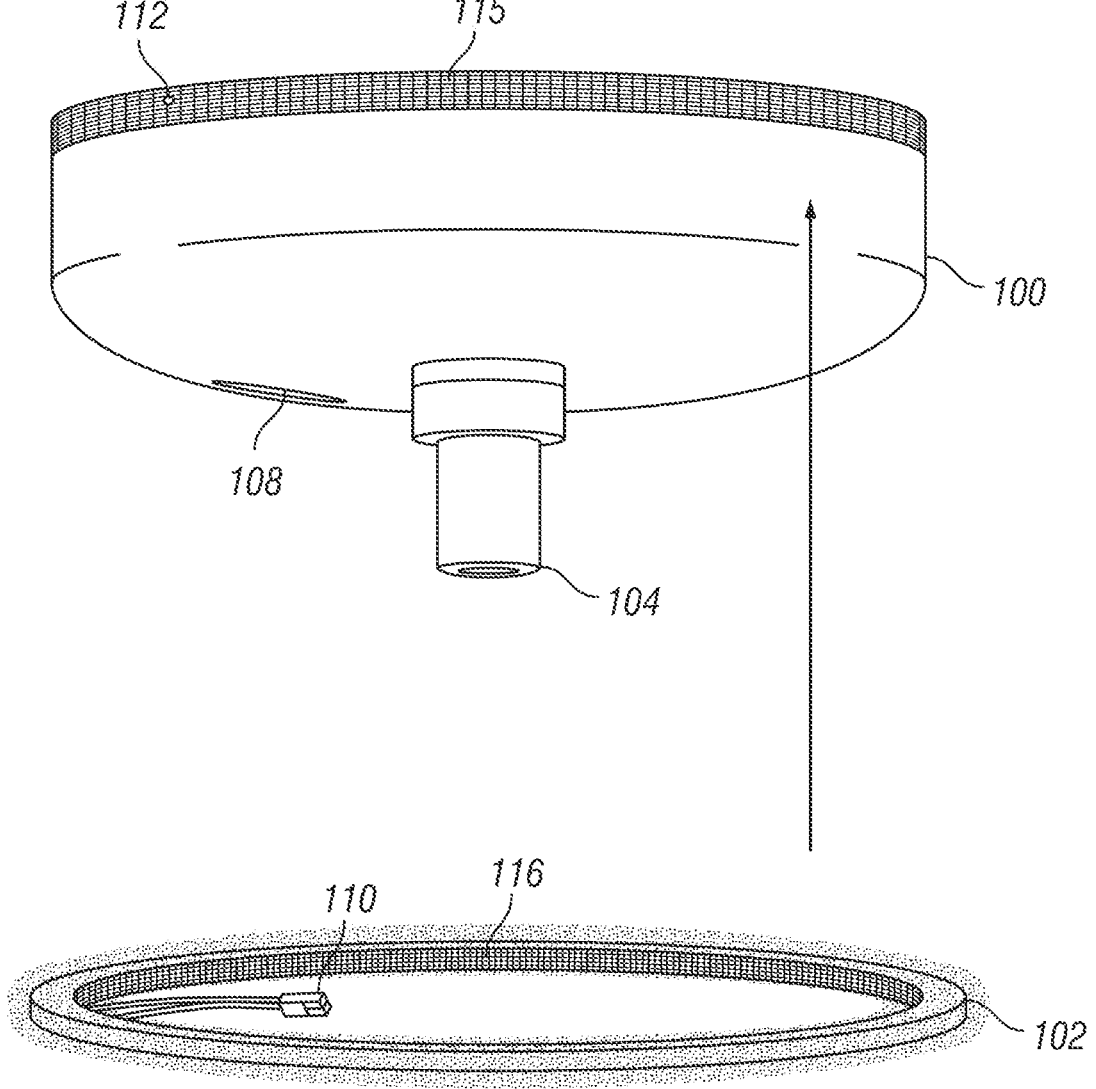
FIG. 3 depicts a second exemplary mechanism for attaching the UV disinfecting ring.
Figure 4:
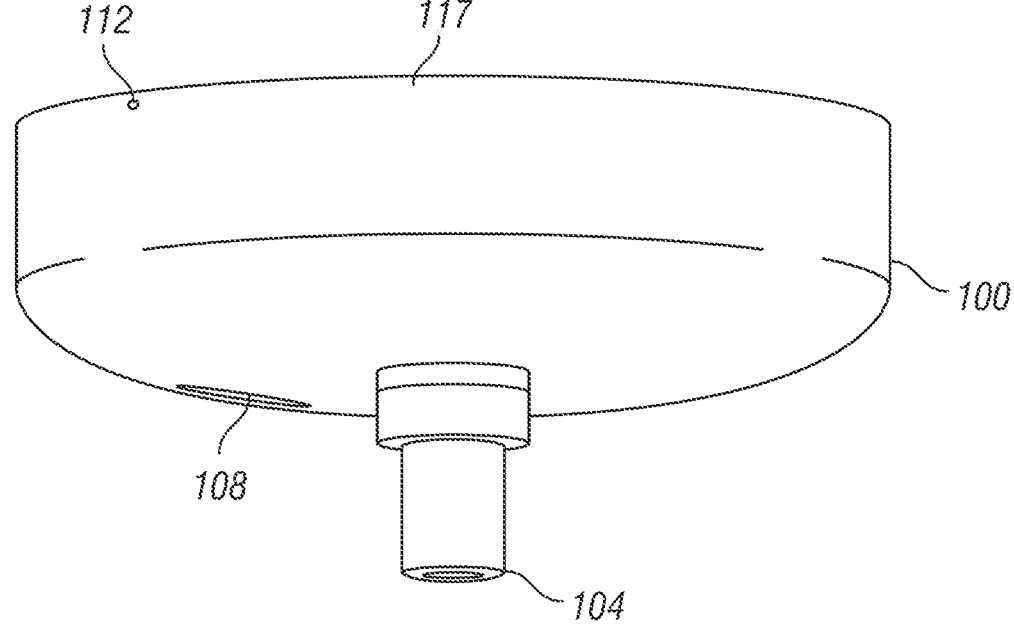
FIG. 4 depicts a third exemplary mechanism for attaching the UV disinfecting ring.
Figure 4:
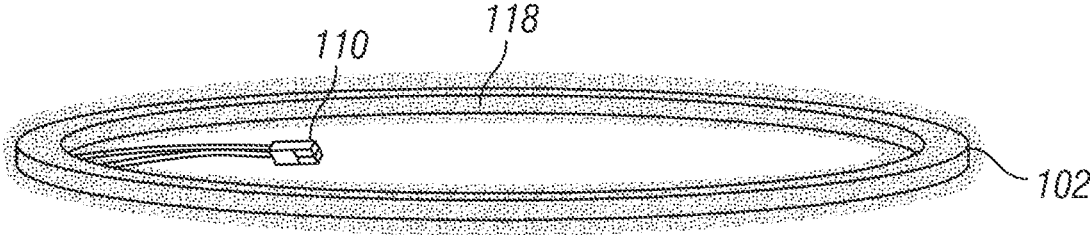
Figure 5:
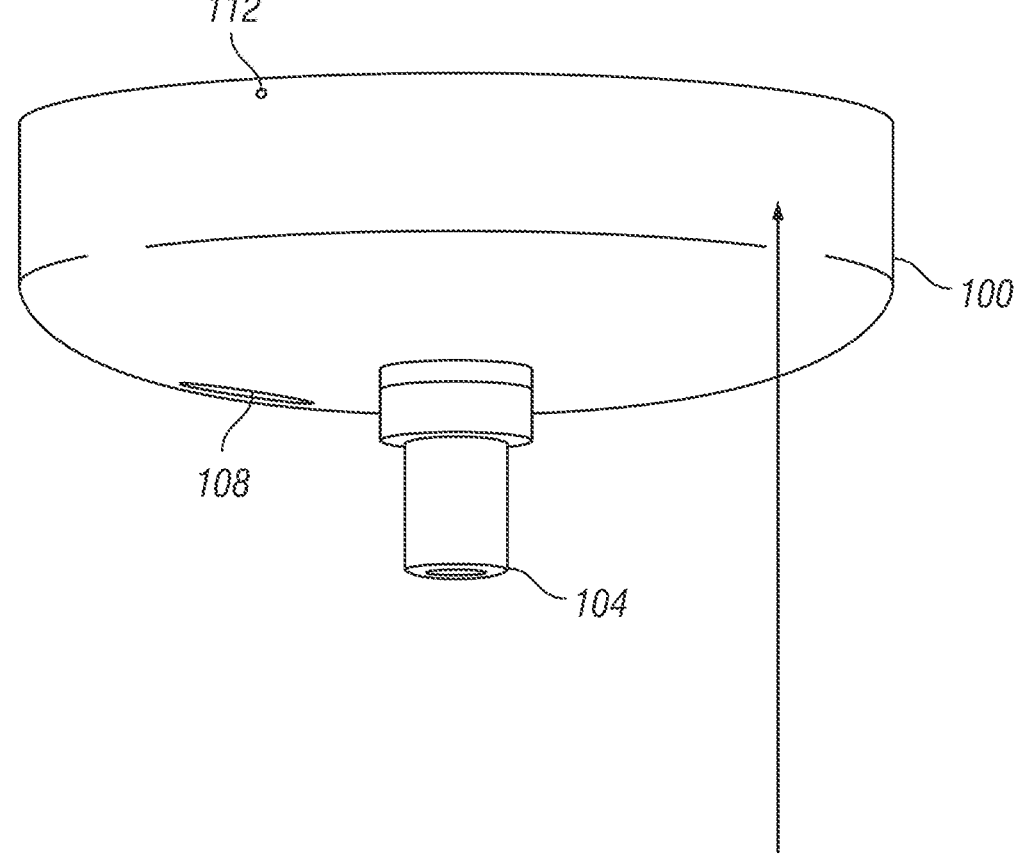
FIG. 5 depicts a fourth exemplary mechanism for attaching the UV disinfecting ring.
Figure 5:
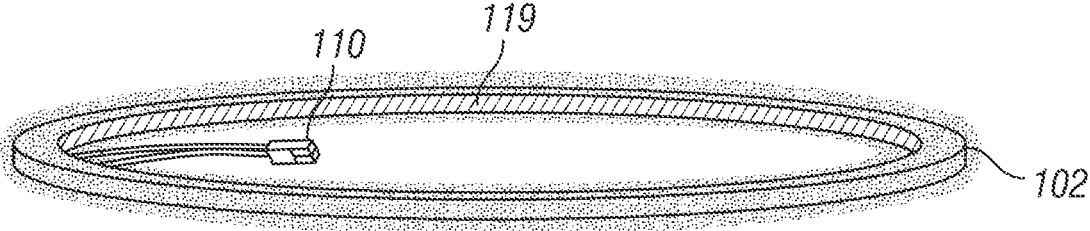

FIGS. 2-5 show various exemplary manners in which disinfecting ring 102 can be removably attached to canopy 100. These include but are not limited to a threading mechanism (FIG. 2), hook and loop fasteners (FIG. 3) or other mechanical fasteners, magnetic coupling (FIG. 4), and adhesives (FIG. 5). As shown in FIGS. 2-5, disinfecting ring 102 can be provided with a coupler 110 for electrically connecting disinfecting ring 102. As also shown in FIG. 2, 30) canopy 100 can be provided with an aperture 112 through which coupler 110 can be inserted to connect with an electrical power supply to energize disinfecting ring 102.

With reference to FIG. 2, canopy 100 includes threading 113 that mates with threading 114 on disinfecting ring 102. Threading 113 can be positioned on canopy 100 differently than as shown in FIG. 2, which has threading 113 positioned on canopy 100 so that disinfecting ring 102 is mounted substantially flush to the ceiling or whatever surface canopy 100 is mounted on.

With reference to FIG. 3, canopy 100 includes one of a hook and loop fastener 115 that releasably engages with the other of the hook and loop fastener 116 on disinfecting ring 102. Hook/loop fastener 115 can be positioned on canopy 100 differently than as shown in FIG. 3, which has hook/loop fastener 115 positioned on canopy 100 so that disinfecting ring 102 is mounted substantially flush to the ceiling or whatever surface canopy 100 is mounted on.

With reference to FIG. 4, canopy 100 is either made of a ferromagnetic material, includes one or more portions that are ferromagnetic, or includes one or more magnetic sections 117. Disinfecting ring 102 has a portion 118 that includes a ferromagnetic material or includes one or more magnets. If canopy 100 is made of a ferromagnetic material, disinfecting ring 102 can be positioned on canopy 100 as desired. Alternatively, magnetic sections 117 can be located on canopy 100 so that disinfecting ring 102 is positioned on canopy 100 as desired.

With reference to FIG. 5, disinfecting ring 102 includes an adhesive material 119 for affixing disinfecting ring 102 to canopy 100. In another embodiment, canopy 100 can have the adhesive material 126 in addition to or instead of disinfecting ring 102.

Figures 6A, 6B, 6C:
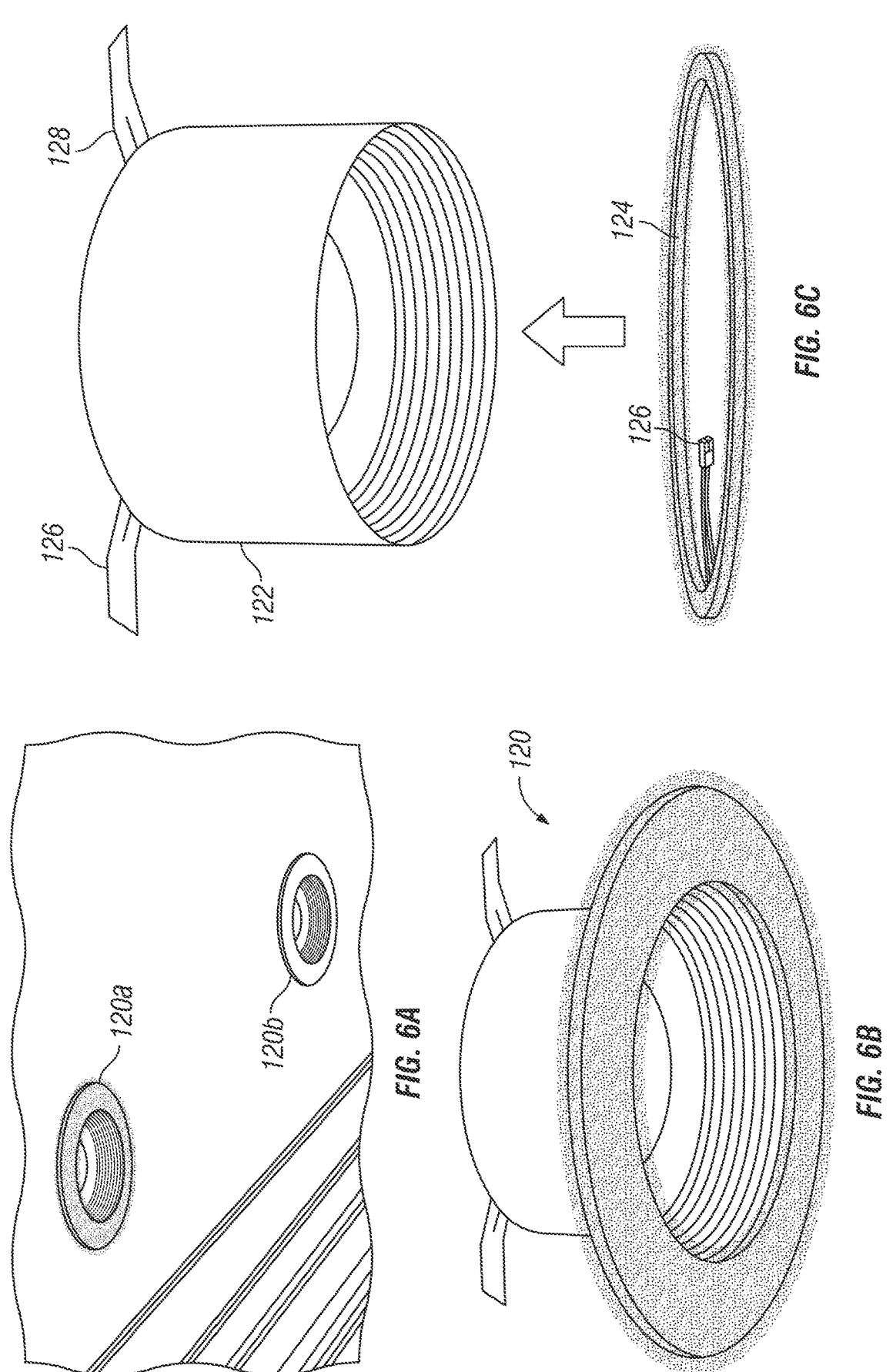
FIGS. 6A-6C depict a recessed lighting fixture with a UV disinfecting ring according to the disclosure.

FIGS. 6A-6C show a recessed lighting fixture 120 that includes a housing 122 and a trim 124 that includes at least a portion with a disinfecting ring. Trim 124 includes a coupler 126 for electrically connecting the disinfecting ring of trim 124. As is well-known, recessed lighting fixture 120 includes tabs 128 for retaining recessed lighting fixture 120 in the ceiling hole. PCT International Application No. PCT/US2018/021919 filed Mar. 12, 2018 and PCT International Application No. PCT/US2021/020233 filed Mar. 1, 2021, both of which are incorporated by reference, disclose embodiments of recessed lighting fixture 120 that include a quick connect device.

Although the disinfecting ring of trim 124 can include any suitable source of UV radiation, in an exemplary embodiment the UV radiation source is an LED array. In one embodiment, the emitted UV radiation is UV-A or FAR UV-C so that the disinfecting ring can emit the radiation regardless of whether a human is exposed to the emitted UV radiation (e.g, an occupied room) or not (e.g, an unoccupied room). In another embodiment, the emitted UV radiation is UV-C so that the disinfecting ring should only emit the radiation if there is no human exposure to the emitted UV radiation (e.g, an occupied room). In this regard, FIG. 6A shows two recessed 30) lighting fixtures 120a, 120b with recessed lighting fixture 120a having an activated LED array and the LED array of recessed lighting fixture 120b not activated.

Figure 7B:
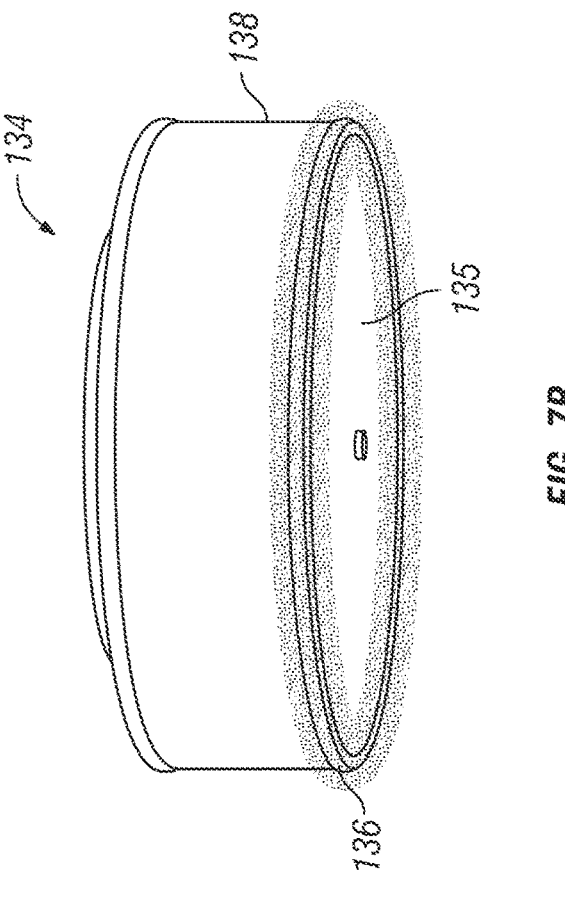
FIGS. 7A and 7B depict flush mount fixtures with disinfecting rings.
Figure 7A:
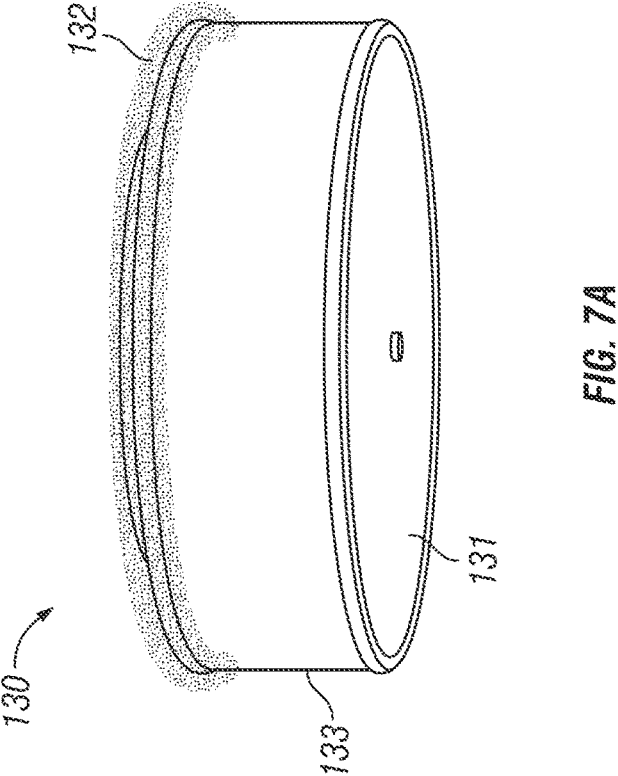

FIGS. 7A and 7B show two versions of a flush mount fixture with a disinfecting ring. For fixture 130, disinfecting ring 132 is found proximal the ceiling mount and visible light for illumination comes from transparent or translucent lens 131, with a light source located inside fixture 130. If desired, side surface 133 can also be transparent or translucent to allow the passage of light. For fixture 134, disinfecting ring 136 is found distal the ceiling mount and visible light for illumination comes from transparent or translucent lens 135, with a light source located inside fixture 134. If desired, side surface 138 can also be transparent or translucent to allow the passage of light. As the location of the disinfecting ring can affect disinfection, the fixture can be selected depending on the application.

Although disinfecting ring 132, 136 can include any suitable source of UV radiation, in an exemplary embodiment the UV radiation source is an LED array. In one embodiment, the emitted UV radiation is UV-A or FAR UV-C so that the disinfecting ring can emit the radiation regardless of whether a human is exposed to the emitted UV radiation (e.g, an occupied room) or not (e.g, an unoccupied room). In another embodiment, the emitted UV radiation is UV-C so that the disinfecting ring should only emit the radiation if there is no human exposure to the emitted UV radiation (e.g, an occupied room).

Figure 8:
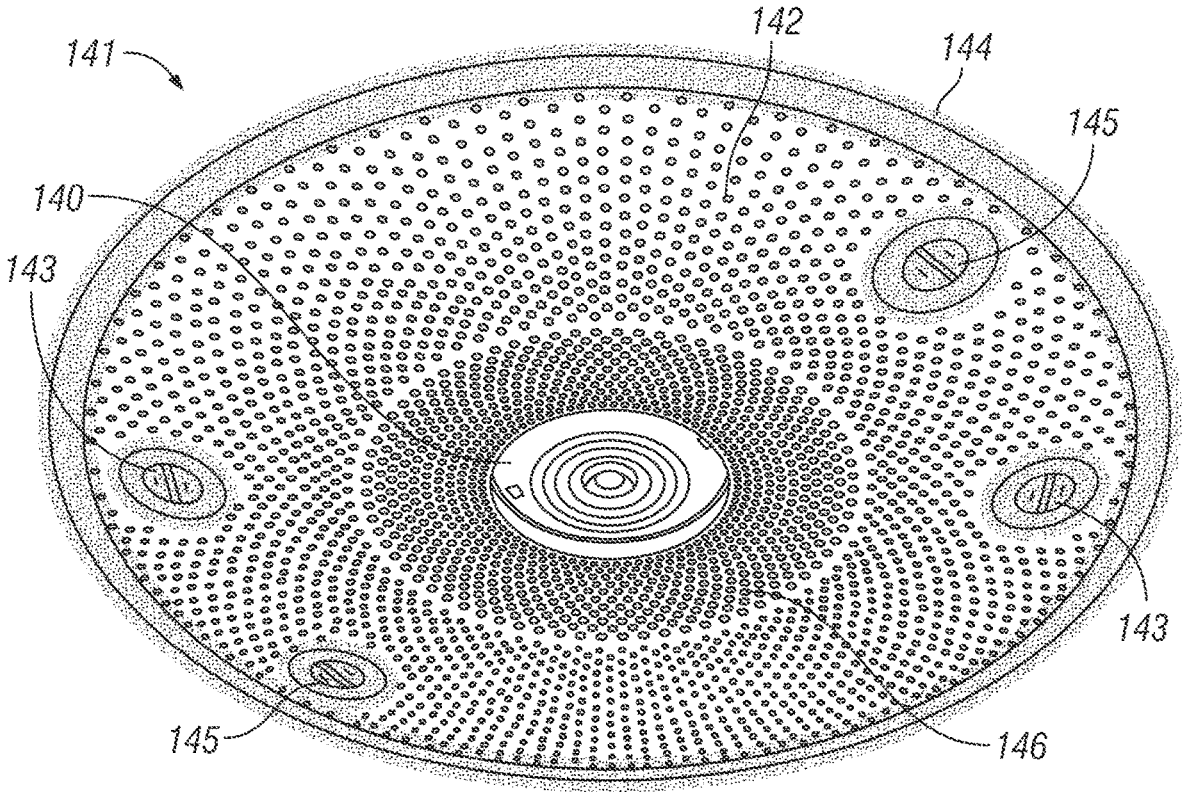
FIG. 8 depicts a socket of a smart quick connect device with a UV-C disinfecting assembly and a UV-A disinfecting ring.

FIG. 8 depicts a socket 140 of a smart quick connect device 141 with central UVC emitters 142 and a UVA disinfecting ring 144. Smart quick connect device 141 may include one or more sensing units 143 for wirelessly communicating a sensed condition. Alternatively or in addition, smart quick connect device 141 can include one or more sensing units 145 for wirelessly receiving a signal. The signal can be a command signal to control smart quick connect device 141, the associated electrical fixture (via socket 140), and/or UVC emitters 142 and disinfecting ring 144. The command signal can be independent of or as a result of the sensed condition.

Although sensing units 143, 145 can have microphone, speaker, or both microphone and speaker functions, smart quick connect device 141 can include a separate speaker/microphone assembly 146.

Sensing units 143, 145 can function to provide the sensing, communications, transmission, and other functions as described herein. These functions can include any or all of, for example, BLUETOOTH communication of information: WiFi communication, for example with a function of hub, router, access point, or relay: a motion sensor to detect movement, or an infrared, sound, and/or heat sensor to detect the presence of humans or animals, useable for example to control an HVAC system or to provide input for an alarm or monitoring system: thermostat: camera for communication, or for an alarm or monitoring system: speaker: smoke detector: fire detector: occupancy detector using any of a variety of appropriate sensors, such as motion, infrared, audio, image detection, image recognition, or air pressure: humidity sensor, for example to protect art or identify leaks or water intrusion; and a power consumption meter to detect intrusion or to improve efficiency; and smoke and/or air quality sensors. Herein, for brevity, the terms 'sensing unit and sensor' are used to collectively refer to any device which can carry out one or more of the foregoing functions, and it should therefore be understood that a 'sensing unit' or 'sensor' herein can sense a condition, actuate, transmit, receive, both send and receive, or is otherwise configured to carry out any of the foregoing functions.

Devices of the disclosure equipped with sensing units 143, 145 can form part of a "smart home" architecture and operation, such as are made by GE and other companies. Accordingly, the electronic board(s) of sensing unit 143, 145 can be provided with electronic circuitry, including an electronic processor, memory, storage, and other components which can enable programming and remote operation associated with such a function. Remote operation can include a central programming or control program which controls the functioning of a device of the disclosure. This can include, for example, control from a website, or control from an app executing upon a smartphone or tablet. Alternatively, a handheld TV/DVR style remote control device can be used.

Devices of the disclosure can include one more sensors which can function as any or all of intelligent thermostats, intelligent hazard-detection unit, intelligent entryway-interface device, smart switch, including smart wall-like switches, smart utilities interface or interface to other service, such as smart wall-plug interface, and a wide variety of intelligent, multi-sensing, network-connected appliances, including refrigerators, televisions, washers, dryers, lights, audio systems, intercom systems, mechanical actuators, wall air conditioners, pool-heating units, irrigation systems, and many other types of intelligent appliances and systems.

Devices of the disclosure can include one or more different types of sensors, one or more controllers and/or actuators, and one or more communications interfaces that connect the smart-home devices to other smart-home devices, routers, bridges, and hubs within a local smart-home environment, various different types of local computer systems, and to the Internet, through which a smart-home device may communicate with cloud-computing servers and other remote computing systems. Data communications can be carried out by sensors 143, 145 and the electronics board(s) associated therewith using any of a large variety of different types of communications media and protocols, including wireless protocols, such as Wi-Fi, ZigBee, 6LoWPAN, various types of wired protocols, including CAT6 Ethernet, HomePlug, and other such wired protocols, and various other types of communications protocols and technologies. Devices of the disclosure can integrate with each other, or with previously known so-called 30) "smart-home" devices, and may themselves operate as intermediate communications devices, such as repeaters, for smart-home devices and other devices of the disclosure. A smart-home environment including devices of the disclosure can additionally include a variety of different types of legacy appliances and devices which lack communications interfaces and processor-based controllers.

A partial list of input sensors 145 that can be incorporated into the various devices of the disclosure includes, but is not limited to, the following examples;

a. zero voltage crossing-used to determine when to trigger TRIACs/IGBTs to control power delivered to attached loads;

b. communications (WiFi, Bluetooth, nRF24)-used to wirelessly receive incoming commands from remote control of output devices, and wifi repeaters;

c. microphone-used for room occupancy detection, or for voice recognition, including carryout out commands by voice;

d. motion detection used for room occupancy detection or intrusion, and to issue or signal an alarm;

e. temperature and humidity sensors-used to make heating/cooling changes;

f. smoke and/or gas detectors, including detectors responsive to the presence of carbon monoxide (CO), propane and other fuels, radon, or any other gas or volatile element, and which can be used to signal or provide an alarm, and which can be used to take emergency/warning actions;

g. glass breakage detectors-used to control security devices;

h. detectors for dangerous substances;

i. a light dimmer;

j. sensors for detecting movement or sounds, including for example waving or clapping or other noises, which can be used to change a light level or other environmental parameter.

A partial list of output sensors 143 includes, but is not limited to, the following: A, triacs/IGBTs used to control fan and lights:

B. communications (WiFi, Bluetooth, nRF24), used to transmit status or convey emergency situations, or to relay information:

C. security camera: used to capture and forward images when triggered by various input sources, including for example a 360 degree camera; and D. emergency backup light: used to provide minimal lighting in emergency situations.

These output sensors 143 can be activated based upon connected input sources 145, or by remote commands received from a communications circuit associated with the device of the disclosure. In some cases, sensors 143, 145 operate as both input and output devices. Additionally, it should be understood that other input, output, or combination devices exist, or which may be hereinafter developed, which can be incorporated into smart quick connect device 141 of the disclosure, and that the foregoing list contains only a few such examples.

Figure 9A:
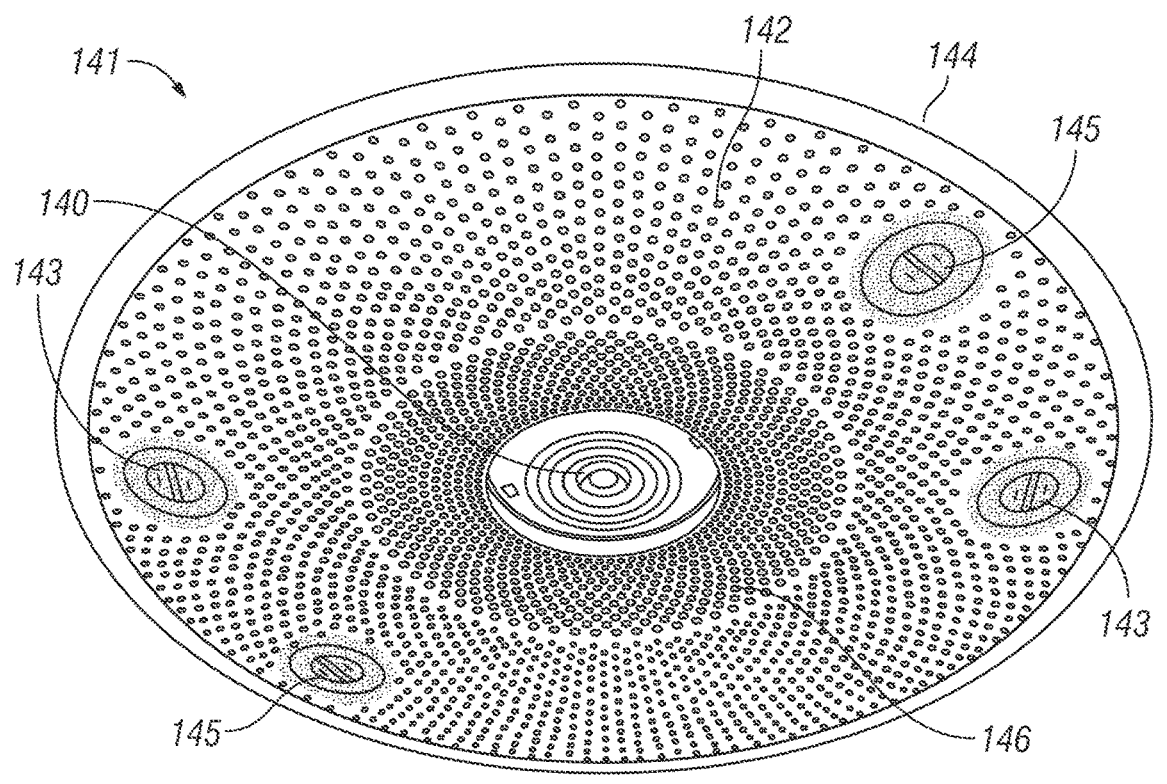
FIGS. 9A and 9B depict the socket of the smart quick connect device of FIG. 8 with the UV-C disinfecting assembly (FIG. 9A) and the UV-A disinfecting ring (FIG. 9B) selectively activated.
Figure 9B:
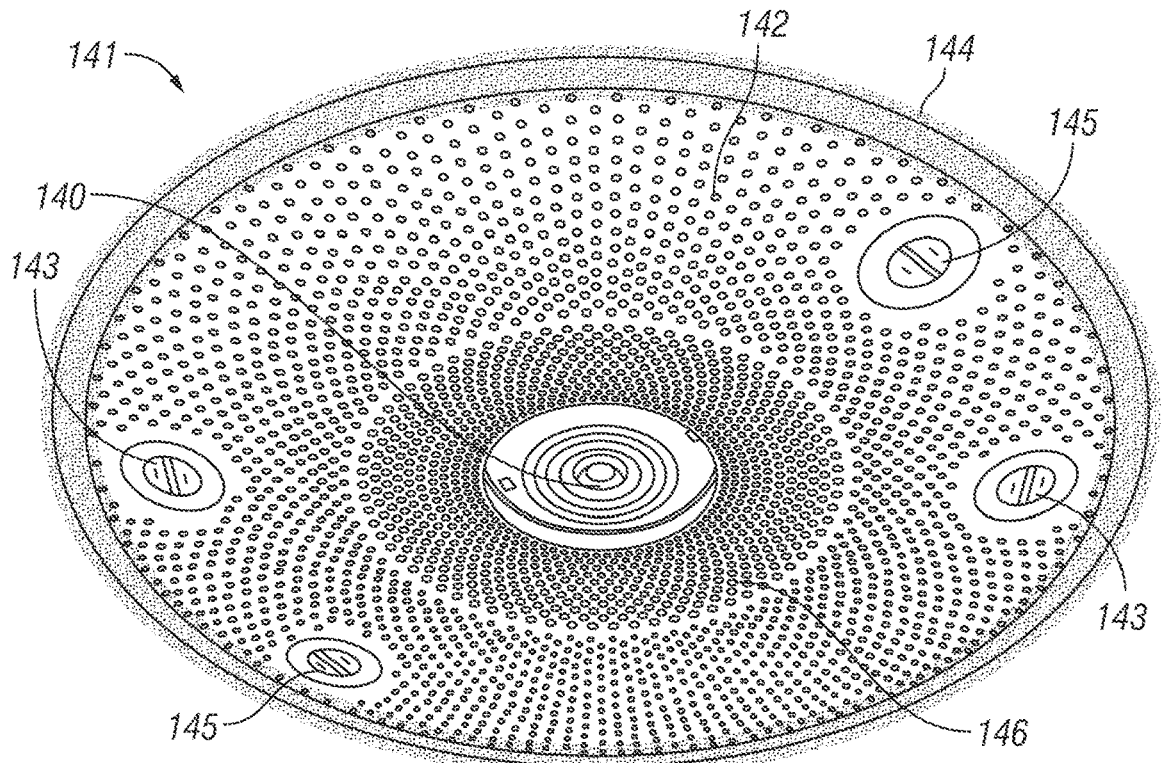

As shown in FIGS. 9A and 9B, central UVC emitters 142 and UVA disinfecting ring 144 can be selectively activated and deactivated. Such selective activation and deactivation can be useful if different wavelengths and treatments are applied by central UVC emitters 142 and UVA disinfecting ring 144. In this regard, the disclosure contemplates that emitters 142 and disinfecting ring 144 can be switched (i.e. emitters 142 emit UVA and disinfecting ring 144 emits UVC).

Although emitters 142 and disinfecting ring 144 can include any suitable source of UV radiation, in an exemplary embodiment the UV radiation source is an LED array. In one embodiment, the emitted UV radiation of disinfecting ring 144 is UV-A or FAR UV-C so that disinfecting ring 144 can emit the radiation regardless of whether a human is exposed to the emitted UV radiation (e.g, an occupied room) or not (e.g, an unoccupied room) and the emitted UV radiation of emitters 142 is UV-C so that emitters 142 should only emit the radiation if there is no human exposure to the emitted UV radiation (e.g, an occupied room).

Figures 10A, 10B:
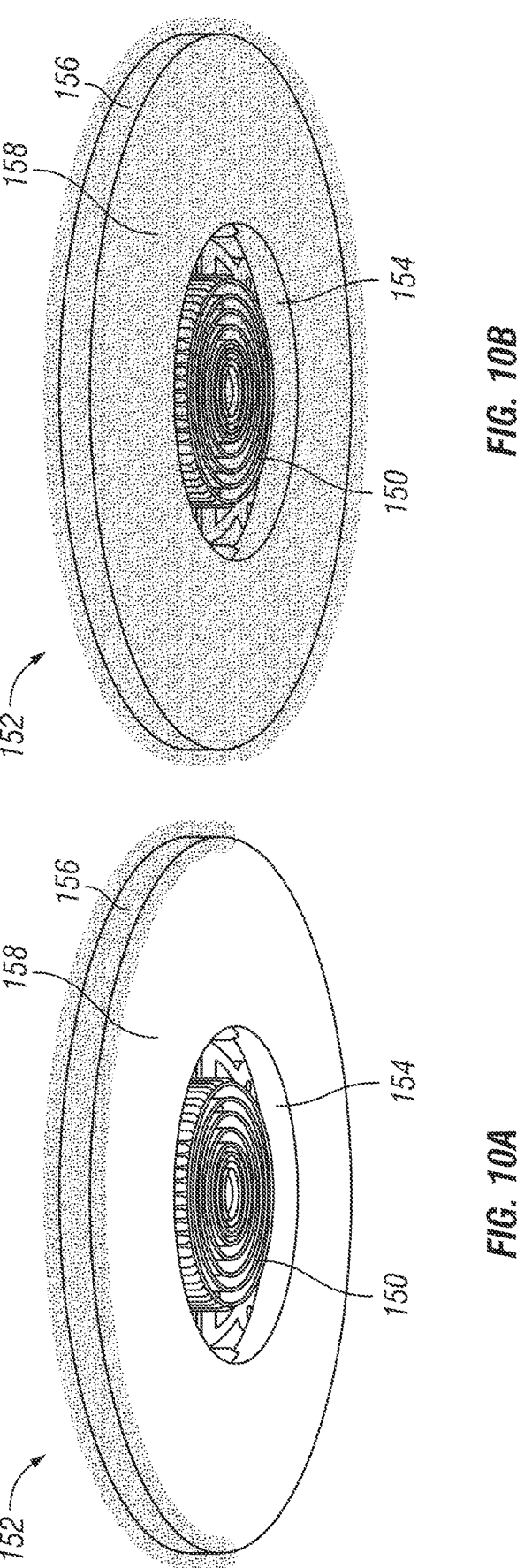
FIGS. 10A and 10B depict another embodiment of a socket of a smart quick connect device with a UV-C disinfecting assembly and a UV-A disinfecting ring.

FIGS. 10A and 10B depict a socket 150 of a smart quick connect device 152. In addition to socket 150, smart quick connect device 152 includes a body 154 with a peripheral disinfecting ring 156 and embedded disinfecting UV emitters 158.

As was the case for smart quick connect device 141, smart quick connect device 152 may include one or more sensing units (analogous to sensing units 143) for wirelessly communicating a sensed condition. Alternatively or in addition, smart quick connect device 152 can include one or more sensing units (analogous to sensing units 145) for wirelessly receiving a signal. The signal can be a command signal to control smart quick connect device 152, the 20) associated electrical fixture (via socket 150), and/or emitters 158 and disinfecting ring 156. The command signal can be independent of or as a result of the sensed condition. Although these sensing units can be positioned in any suitable location of smart quick connect device 152, in an exemplary embodiment, the sensing units are located within or on body 154.

FIG. 10A shows only disinfecting ring 156 activated and FIG. 10B shows both disinfecting ring 156 and embedded UV emitters 158 activated. As these figures illustrate, embedded emitters 158 and disinfecting ring 156 can be selectively activated and deactivated. Such selective activation and deactivation can be useful if different wavelengths and treatments are applied by emitters 158 and disinfecting ring 156. In an exemplary embodiment, emitters 158 emit UVC radiation and disinfecting ring 156 emits UVA and/or FAR UVC radiation.

However, the disclosure contemplates that emitters 158 and disinfecting ring 156 can be switched (i.e. emitters 158 emit UVA and/or FAR UVC and disinfecting ring 156 emits UVC). Although emitters 158 and disinfecting ring 156 can include any suitable source of UV radiation, in an exemplary embodiment the UV radiation source is an LED array. In one embodiment, the emitted UV radiation of disinfecting ring 156 is UV-A or FAR UV-C so that disinfecting ring 156 can emit the radiation regardless of whether a human is exposed to the emitted UV radiation (e.g, an occupied room) or not (e.g, an unoccupied room) and the emitted UV radiation of emitters 158 is UV-C so that emitters 158 should only emit the radiation if there is no human exposure to the emitted UV radiation (e.g, an occupied room).

Figure 11B:
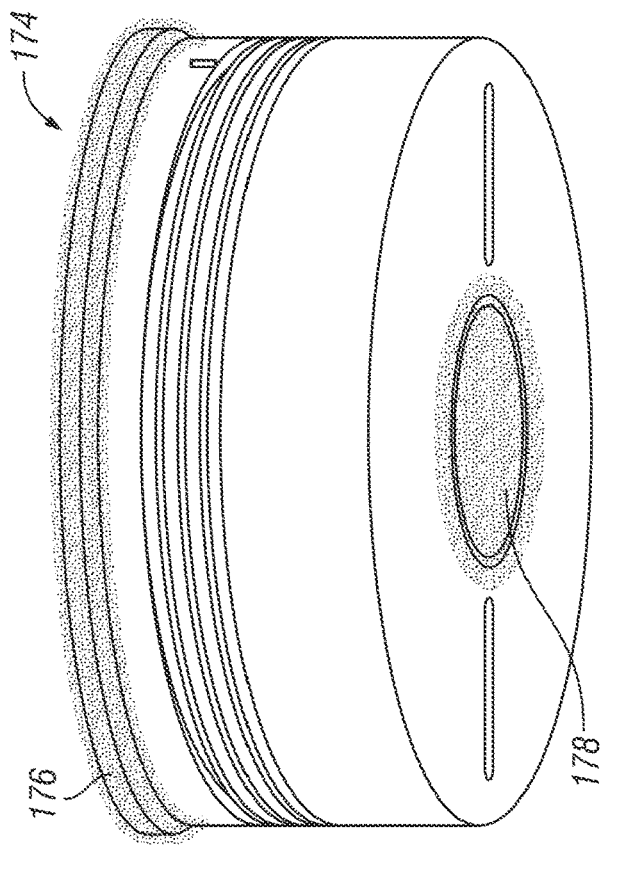
FIGS. 11A and 11B depict a smoke and $CO_2$ detector with a UV disinfecting ring (FIG. 11A) and with an integrated disinfecting central portion and disinfecting ring (FIG. 11B).
Figure 11A:
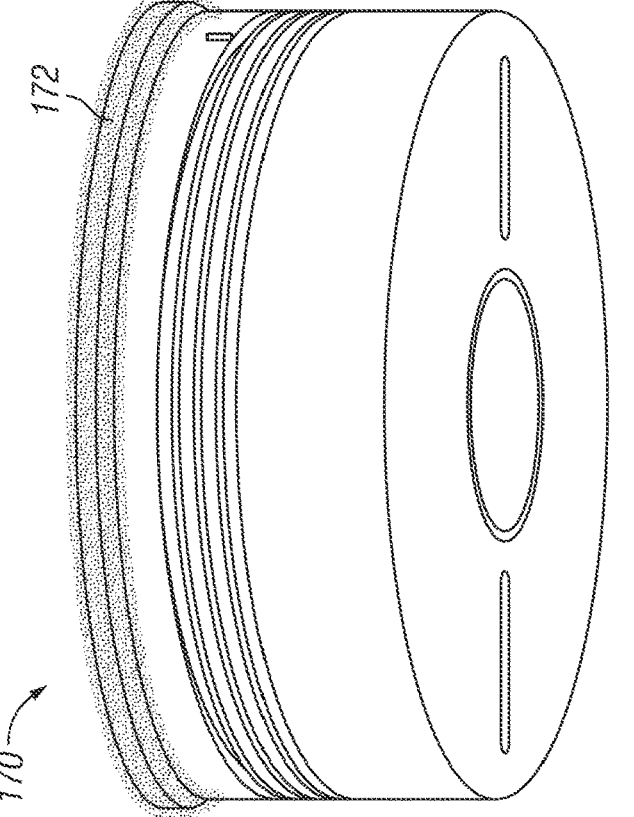

FIGS. 11A and 11B depict two versions of combined smoke and $CO_2$ detectors. Detector 170 includes a disinfecting ring 172 (with a structure and function substantially similar to previously described disinfecting ring 102, 132, 136, 144, 156). Detector 174 includes a disinfecting ring 176 (also with a structure and function substantially similar to previously described disinfecting ring 102, 132, 136, 144, 156) and an UV emitter 178 that is operable separately from disinfecting ring 176.

Although emitter 178 and disinfecting ring 176 (as well as disinfecting ring 172) can include any suitable source of UV radiation, in an exemplary embodiment the UV radiation source is an LED array. In one embodiment, the emitted UV radiation of disinfecting ring 172, 176 is UV-A or FAR UV-C so that disinfecting ring 172, 176 can emit the radiation regardless of whether a human is exposed to the emitted UV radiation (e.g, an occupied room) or not (e.g. an unoccupied room) and the emitted UV radiation of emitter 178 is UV-C so that emitter 178 should only emit the radiation if there is no human exposure to the emitted UV radiation (e.g, an occupied room)

For detector 174, emitter 178 and disinfecting ring 176 can be selectively activated and deactivated. Such selective activation and deactivation can be useful if different wavelengths and treatments are applied by emitter 178 and disinfecting ring 176. In an exemplary embodiment as set forth above, emitter 178 emits UVC radiation and disinfecting ring 176 emits UVA and/or FAR UVC radiation. However, the disclosure contemplates that emitter 178 and disinfecting ring 176 can be switched (i.e. emitter 178 emits UVA and/or FAR UVC and disinfecting ring 176 emits UVC).

In an exemplary embodiment, emitter 178 also includes an array of visible light that actuates to provide visual warning in addition to audible warning with detector 174 detects smoke and/or $CO_2$.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

What is claimed is:

1. A canopy for a light fixture, wherein the canopy includes
a connector for coupling to the light fixture,
a plug of a quick connect device, and
a plurality of emitters on the canopy emitting UVA and/or FAR UVC radiation; and
wherein the canopy is between the plurality of emitters and the light fixture.

2. The canopy of claim 1, wherein the plurality of emitters forms a ring on a periphery of the canopy.

3. The canopy of claim 2, wherein the plurality of emitters is an array of LEDs.

4. The canopy of claim 3, wherein the array of LEDs emits UVA radiation.

5. The canopy of claim 4, further comprising an antenna and/or sensor array to control selective activation of the plurality of emitters and/or illumination of the light fixture.

6. The canopy of claim 5, wherein the plurality of emitters is removably attached to the canopy.

7. The canopy of claim 6, wherein the removable attachment is achieved with at least one of a screw connection, a hook and loop fastener, a magnetic coupling, and an adhesive.

8. The canopy of claim 7, wherein the removable attachment is at a base of the canopy.

9. The canopy of claim 7, wherein the plurality of emitters includes a coupler for supplying electricity thereto and the canopy includes an aperture for accommodating the coupler.

10. A smart quick connect device for electrically and mechanically connecting an electrical fixture, the device comprising
a socket and
a plurality of emitters on the socket emitting UV radiation;
wherein the plurality of emitters includes a first plurality of emitters in the form of a ring along a periphery of the smart quick connect device and a second plurality of emitters centrally located within the ring on the smart quick connect device.

11. The smart quick connect device of claim 10, wherein the first and second plurality of emitters are separately activatable.

12. The smart quick connect device of claim 11, wherein the first plurality of emitters emits UVA and/or FAR UVC radiation when activated and the second plurality of emitters emits UVC radiation when activated.

13. The smart quick connect device of claim 12, wherein the first plurality of emitters comprises a first array of LEDs and the second plurality of emitters comprises a second array of LEDs.

14. The smart quick connect device of claim 13, wherein the first array of LED's emits UVA radiation when activated.

15. The smart quick connect device of claim 12, wherein the first plurality of emitters emits UVA radiation when activated.

16. The smart quick connect device of claim 15, further comprising at least one sensing unit for wirelessly communicating a sensed condition and/or for wireless receiving a signal.

17. The smart quick connect device of claim 16, wherein the at least one sensing unit includes a sensor for wirelessly receiving a command signal to control the device and/or an associated electrical fixture.

18. The smart quick connect device of claim 17, wherein the sensor controls activation of the first and second plurality of emitters.

19. The smart quick connect device of claim 18, wherein the command signal results from the sensed condition.

* * * * *